United States Patent [19]

Eisenhardt et al.

[11] Patent Number: 4,544,455
[45] Date of Patent: Oct. 1, 1985

[54] SALT BRIDGE LIQUID

[75] Inventors: Anne R. Eisenhardt, Birkerød; Ole J. Jensen, Søborg, both of Denmark

[73] Assignee: Radiometer A/S, Copenhagen, Denmark

[21] Appl. No.: 495,262

[22] Filed: May 17, 1983

[30] Foreign Application Priority Data

May 17, 1982 [DK] Denmark .......................... 2206/82

[51] Int. Cl.$^4$ ............................................ G01N 27/46
[52] U.S. Cl. .................................. 204/1 T; 204/403; 204/416; 204/418; 204/420; 204/435
[58] Field of Search ............... 204/435, 403, 416-420, 204/1 T

[56] References Cited

U.S. PATENT DOCUMENTS

| | | | |
|---|---|---|---|
| 3,556,950 | 1/1971 | Dahms | 204/435 |
| 3,833,495 | 9/1974 | Grubb | 204/435 |
| 3,874,850 | 4/1975 | Sorensen et al. | 204/1 T |
| 3,972,614 | 8/1976 | Johansen et al. | 356/36 |
| 3,997,420 | 12/1976 | Buzza | 204/420 |
| 4,160,714 | 7/1979 | Andersen | 204/411 |

OTHER PUBLICATIONS

Grove-Rasmussen, "Acta Chemica Scandinavia", vol. 5, 1951, pp. 422-430.
Ole Siggaard-Anderson, "The Acid-Base Status of the Blood", 4th Rev. Ed., 1974, p. 156.
Orion Research Inc. Newsletter/Specific Electrode Technology, vol. 1, No. 4, Sep. 1969, pp. 21-23.
Linnet, "pH Measurements in Theory and Practice", 1. edition, 1970, pp. 60-64.
European Search Report, dated 3/08/83.

Primary Examiner—T. Tung
Attorney, Agent, or Firm—Stiefel, Gross, Kurland & Pavane

[57] ABSTRACT

Salt bridge liquid for use in potentiometric measurement of blood or a blood liquid.

The salt bridge liquid contains $Na^+$-ions and $HCOO^-$-ions in substantially equimolar amounts, preferably in a concentration larger than or equal to 1 M, in particular about 4 M.

When this salt bridge liquid is used, the potentiometric measurement will give corresponding results when measuring a blood sample and the corresponding plasma sample because the suspension effect which is caused by the erythrocytes and which is seen when using other salt bridge liquids is substantially eliminated. Furthermore, different blood samples with the same ion concentration but with varying erythrocyte content will give corresponding measuring results.

6 Claims, 8 Drawing Figures

SALT BRIDGE LIQUID

FIELD OF INVENTION

The present invention relates to the use of a particular solution as salt bridge liquid in potentiometric measurement of blood or blood liquid.

BACKGROUND OF INVENTION

It is well known and also described in the literature that in potentiometric measurement of a whole blood sample and the corresponding plasma sample, deviating measuring results are often recorded between the two samples, and that this deviation is dependent on the erythrocyte content of the whole blood sample. This effect is usually called the suspension effect, cf. e.g. O. Siggaard Andersen, The Acid-Base Status of Blood, Munksgaard, Copenhagen, 1974, p. 156.

The deviating measuring results, which e.g. occur for a potentiometric measuring chain comprising sample, an ion-sensitive indicator electrode, a reference electrode and saturated KCl as salt bridge liquid between the sample and the reference electrode, are explained by the fact that the liquid junction potential between a whole blood sample and the salt bridge liquid is different from the liquid junction potential between a corresponding plasma sample and the salt bridge liquid.

The influence of the liquid junction potential on the measuring result obtained by potentiometric determination appears from the Nernst equation, which expresses the connection between the concentration of the ion I and the potential E of the electrode chain:

$$E = E_o + E_j + \frac{RT}{ZF} \log c_I$$

in which

E represents the potential of the electrode chain, $E_o$ represents the standard potential of the electrode chain which is independent of the concentration of I, $E_j$ represents the liquid junction potential, RT/ZF is the Nernst factor, and $c_I$ is the concentration of the ion I.

In the present specification and claims, the concentration of the ion I is to be understood as covering both the concentration and the activity of the ion I.

From the above equation it is clear that an electrode chain for which the Nernst equation applies can be used to determine the concentration of I, $c_I$, provided that the electrode chain has first been calibrated with a solution with a known concentration of I and that $E_o + E_j$ can be regarded as constant.

When measuring blood samples which are identical apart from varying erythrocyte content, it must be expected that $E_o$ is constant and that it is thus variations of $E_j$ which account for the suspension effect.

In connection with the reference to the suspension effect in the above-mentioned literature passage by O. Siggaard Andersen, various proposals for the elimination of the effect are given, viz. either to use a 0.15M KCl salt bridge or to insert a small bridge of plasma between blood and saturated KCl. Likewise, the possibility of adjusting for the suspension effect is mentioned.

These proposals each have various disadvantages:

by the normally occurring variations of the ion composition of blood samples, a 0.15M KCl salt bridge will give varying liquid junction potentials, as the liquid potential will then not be dominated by $K^+$- and $Cl^-$-ions because of the low concentration of these ions;

insertion of a plasma bridge is complicated and not convenient for routine measurements of non-scientific character;

corrections can only be made according to a knowledge of the erythrocyte content of the sample, i.e. this requires equipment for the determination of an extra parameter.

Another possibility would be to establish a so-called flow junction in which the salt bridge liquid which contacts the sample is constantly renewed, but this solution is also inconvenient, especially because flow-conditioned potentials will occur.

In connection with the development of instruments for the determination of the potassium ion concentration in blood and plasma, it has been found inconvenient to use a salt bridge with a high content of potassium ions (2-3M) because of the risk that the sample, whose potassium content is about $4 \times 10^{-3}$M, is contaminated.

Therefore, alternative salt bridge liquids have been sought for, and in this connection, the usual criterion has been taken for the basis, viz. that the anion and the cation must have equivalent conductivity of very nearly the same magnitude, cf. e.g. Orion Research Inc., Newsletter/Specific Electrode Technology, Vol. 1, No. 4, September 1969, pages 21-23.

BRIEF DISCLOSURE OF INVENTION

On the basis of table information for a great number of both inorganic and organic anions and cations found in the above-mentioned Orion Research reference, it has now been found that an especially suitable salt bridge liquid in connection with potentiometric measurement of blood or blood liquid is one which contains $Na^+$-ions and $HCOO^-$-ions, preferably in a concentration larger than or equal to 1M, in particular larger than or equal to 1.5M.

DETAILED DESCRIPTION OF INVENTION

With a salt bridge liquid containing $Na^+$-ions and $HCOO^-$-ions, normally in substantially equimolar amounts, the suspension effect may be eliminated to such an extent that the potential variations between a blood sample and the corresponding plasma occurring due to the suspension effect are substantially reduced in comparison with the suspension effect occurring with saturated KCl as salt bridge liquid, and so modest that in measurements when a measuring accuracy of the magnitude 2% is aimed at, it is not necessary to compensate for the suspension effect, even for blood samples with a hemoglobin content of up to 25 g%. Such a hemoglobin content is found in new-born babies, while the range in adults varies about 14 g% (11-17 g%).

Thus, by elimination of the suspension effect, accordance between various samples of the same ion concentration, but of varying erythrocyte content, will also be found.

Expressed in another way, for the purpose of the present invention the suspension effect is considered to be eliminated when a change in the electrode potential of less than 0.3 mV is seen for a variation of the erythrocyte content in a sample corresponding to a variation of the hemoglobin content in the hemolyzed sample of between 0 and 25 g%. For monovalent ions, this implies a measuring error of about 1% and for divalent ions, a measuring error of about 2%.

In the present specification and claims, the expression potentiometric measurement is used as a designation of the determination of the concentration of an ion by means of an ion specific or an ion-sensitive electrode of the type whose potential response follows or essentially follows the Nernst equation.

The expressions blood or blood liquid are used as a designation of whole blood and liquids prepared from whole blood, such as plasma, plasma/erythrocyte mixtures of varying erythrocyte content, and serum.

In blood or blood liquid, the ions whose concentration allows determination by potentiometric measuring methods are above all $K^+$, $Na^+$, $Ca^{++}$, $Mg^{++}$, $Li^+$, $H^+$, $HCO_3^-$ and $Cl^-$.

It is contemplated that the salt bridge liquid used according to the invention has the same effect no matter what liquid junction structure is used, e.g. open liquid junction, porous stick, membrane junction, ground glass junction and the like, cf. e.g. N. Linnet, pH Measurements in Theory and Practice, 1st Ed., Radiometer A/S, Copenhagen 1970, pp. 60–64. Thus, it is also considered probable that the salt bridge liquid is not only applicable in connection with automatic measuring instruments of the type described below where the indicator electrode and the reference electrode are physically separated from one another, but joined through liquid conduits containing sample/salt bridge liquid, but also in so-called combination electrodes where the indicator electrode and the reference electrode are built together in a unity.

It is preferred to use a solution of a not too low ion concentration as salt bridge liquid. An ion concentration larger than or equal to 1M, in particular larger than or equal to 1.5M, is considered to be suitable, and in connection with the testing of the salt bridge liquid of the invention, a 4M solution of HCOONa in water has been tested and proved to be satisfactory. If desired, the viscosity of the salt bridge liquid can be regulated by admixture of a thickening agent.

In particular for use in connection with automatic analysis instruments where the user will often prefer to use ready-mixed salt bridge liquid, it is furthermore preferred to include, in a ready-mixed salt bridge liquid, an active amount of a germicide, e.g. a germicide commercialised under the trade mark DECIQUAM 222 by STRUERS, Copenhagen (didecyldimethylammonium bromide).

The invention also relates to a salt bridge liquid of the above-described kind commercialized for its intended purpose, that is, a solution which contains $Na^+$-ions and $HCOO^-$-ions in substantially equimolar amounts and in a concentration larger than or equal to 1M, and which is packaged with or accompanied by instructions for using it as a salt bridge liquid, in particular for using it as a salt bridge liquid in potentiometric measurement of blood or blood liquid.

The invention further relates to a process of determining the concentration of an ion in a sample of blood or a blood liquid using a measuring chain comprising an ion-sensitive indicator electrode and a reference electrode in which the ion-sensitive indicator electrode is brought into contact with the sample and the reference electrode is brought into contact with a salt bridge liquid which is in contact with the sample through a liquid junction, in which process the salt bridge liquid used contains $Na^+$-ions and $HCOO^-$-ions.

BRIEF DESCRIPTION OF THE DRAWINGS

In the drawings,

FIG. 1 is a diagram of an automatic analysis instrument for potentiometric determination of the $Na^+$- and $K^+$-concentration in physiological liquids such as blood, plasma, urine and the like;

DETAILED DESCRIPTION OF THE DRAWINGS

Figure 1:
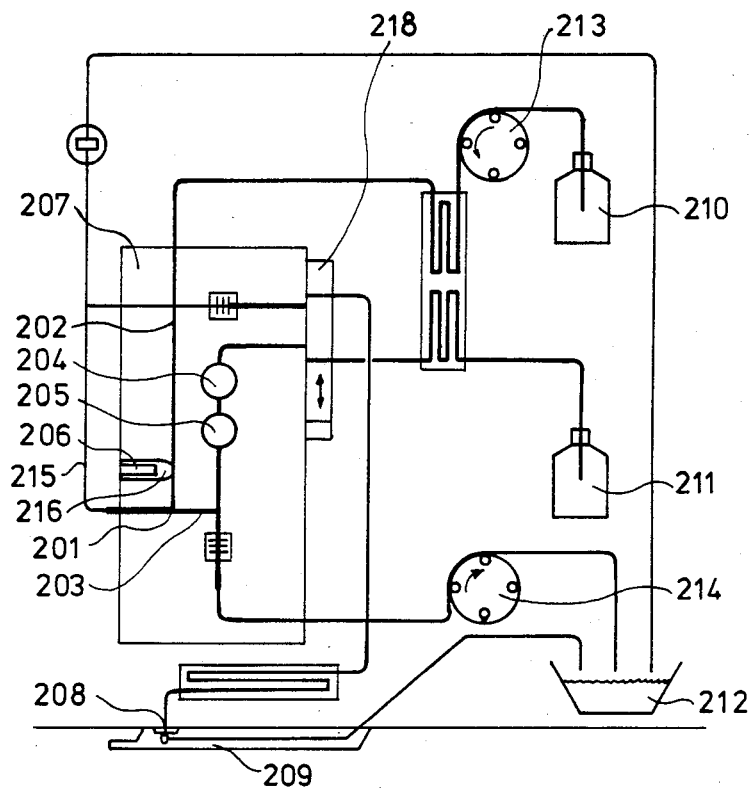

Reference is made to FIG. 1. A measuring block generally designated 207 is designed for receiving a sodium-sensitive glass electrode device in a measuring chamber 205 and a potassium-sensitive electrode device on the basis of valinomycin in a measuring chamber 204 and a reference electrode 206 (closed calomel electrode) in a well 216.

During measurement, an open liquid junction is formed in a contact area 201, where a liquid conduit 202 filled with salt bridge liquid debouches into a liquid conduit 203 filled with sample. In the contact area, the liquid conduits 202 and 203 are constituted by bores of a diameter of 0.8 mm in the measuring block 207, which is made of glass ceramics, MACOR ®, commercialised by CORNING GLASS WORKS, Corning, N.Y., USA, and which is of the type described in the specification of U.S. Pat. No. 4,160,714, the measuring chambers being formed by superficial hollows in the measuring block 207. The instrument receives sample through an inlet 208 after opening of a pivoting flap 209. Calibration liquid can be introduced at the same place. Salt bridge liquid is kept in a reservoir 210 and rinsing fluid, which at the same time functions as a calibration liquid, in a reservoir 211, and the liquids used (salt bridge liquid, rinsing fluid, sample, calibration liquid) are emptied out into a waste receiver 212. A liquid conduit 215 is used for the transport of salt bridge liquid and sample or calibration liquid to the waste receiver after the termination of the measuring or the calibration operation.

The liquid transport in the instrument is controlled by a built-in microcomputer which activates/deactivates two pumps 213 and 214 in dependence of signals received by the microcomputer. A flat tap valve 218 has various positions which also determine the liquid transport in the instrument.

Liquid junction is established by moving sample or calibration liquid to the contact area 201, a continuous liquid string filling the liquid conduit 203 and the measuring chambers 204 and 205. Salt bridge liquid is carried forward in the liquid conduit 202 so that a string of salt bridge liquid is present in front of the reference electrode 206 and up to the contact area 201.

The concentration of the sodium ion and the potassium ion respectively is calculated in the built-in microcomputer of the instrument on the basis of the electrode potentials measured over the sodium-sensitive electrode, the potassium-sensitive electrode and the reference electrode respectively. The electrode potentials used for the calculation are the electrode potentials about 5 or 6 seconds after establishment of liquid junction.

Figure 2:
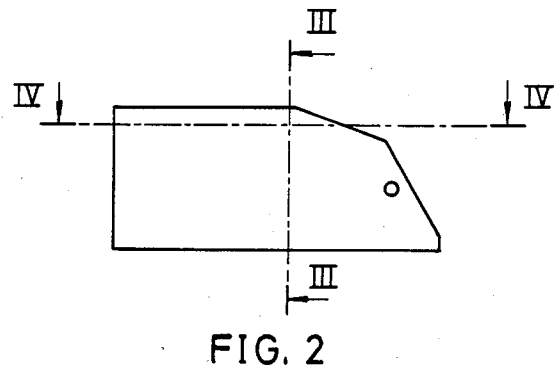

FIG. 2 shows the measuring block 207 shown in diagram in FIG. 1, but seen from the side.

Figure 3:
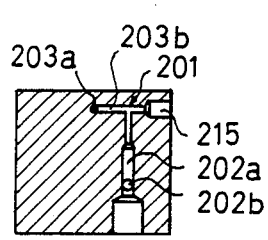
FIGS. 2–5 show the construction of liquid junction in the analysis instrument of FIG. 1 in detail.
Figure 4:
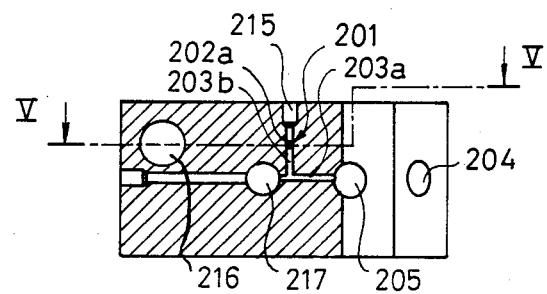
Figure 5:
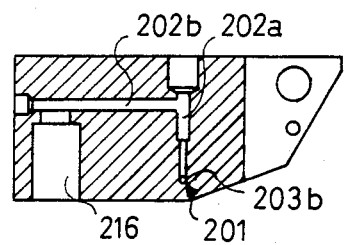

FIGS. 3, 4 and 5 are three sectional views at right angles to each other through the measuring block 207 shown in FIG. 2 in such a manner that the geometry of the liquid junction contact area 201 is shown in detail. In FIGS. 1, 3, 4 and 5, the same reference numbers are used for corresponding parts.

At the establishment of liquid junction, the liquid conduits 203a and 203b contain sample or calibration liquid which in the liquid conduit 203a with the measuring chambers 204 and 205 is in front of the two indicator electrodes. The liquid conduits 202a and 202b contain salt bridge liquid which, in the liquid conduit 202b, is in front of the reference electrode mounted in the well 216 which is also filled up with salt bridge liquid around the reference electrode. In addition, FIG. 4 shows a bore 217 emanating from the upper surface of the measuring block 207 and intended for mounting of a liquid detector of the type disclosed in the specification of published Danish Patent Application No. 229/80.

Figure 6:
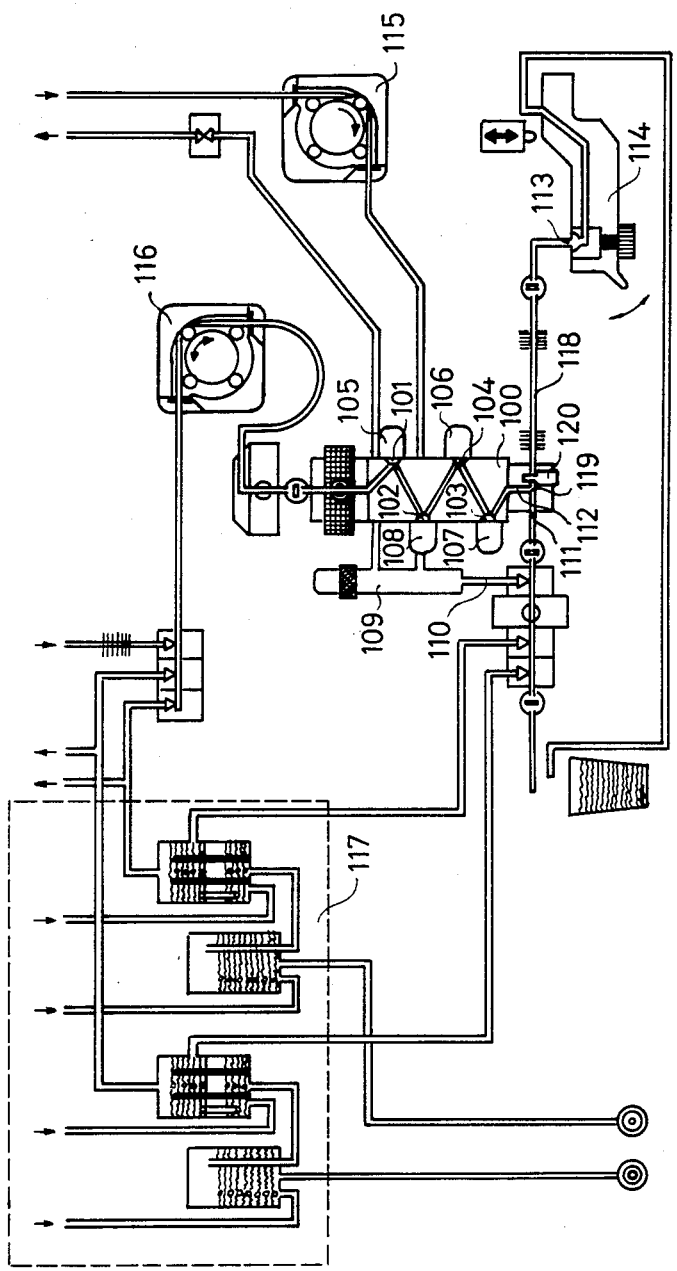
FIG. 6 is a diagram of another analysis instrument e.g. for the determination of pH and the $K^+$-concentration in physiological liquids.

FIG. 6 is a diagram of an automatic analysis instrument for the determination of pH, $P_{O_2}$, $P_{CO_2}$ and the potassium concentration in physiological liquids.

The instrument comprises a measuring block 100 of e.g. glass ceramics. Through a liquid conduit 118 with a liquid sensor 120, the measuring block is connected with a sample inlet 113 provided with a pivoting closing flap 114. In principle, the measuring block is designed as disclosed in the specification of U.S. Pat. No. 4,160,714 and comprises superficial measuring chambers, 101, 102, 103 and 104 which independently are made to receive electrode devices 105, 106, 107 and 108. The electrode device 105 is an electrode device for the determination of the partial pressure of $CO_2$, $P_{CO_2}$; the electrode device 106 is an electrode device for the determination of pH; the electrode device 107 is an electrode device for the determination of the activity or the concentration of potassium ions of the type normally designated a valinomycin electrode, and the electrode device 108 is an electrode device for the determination of the partial pressure of $O_2$, $P_{O_2}$. (The pH, $P_{CO_2}$ and $P_{O_2}$ electrodes are calibrated by means of calibration liquids prepared in calibration towers which are shown diagrammatically at 117 eiyh associated equipment and which are supplied by means of a pump 116). A closed calomel reference electrode is placed in a well 109. During the measuring, the well 109 and liquid conduits 110 and 111 are filled up with salt bridge liquid supplied from a reservoir (not shown) by means of a pump 115, while a liquid conduit 112 is filled up with sample. An open liquid junction 119 is established at the interface between the two liquids where the liquid conduit 112 debouches into the liquid conduit 111. The inner diameter of the liquid conduits 111 and 112 is 1.4 and 0.8 mm respectively.

The instrument is a fully automatic analysis instrument in which calibration, rinsing, measurement, establishment of liquid junction, calculation and reading of measuring results take place automatically. In its construction, the instrument closely corresponds to a blood gas measuring instrument ABL3 produced by RADIOMETER A/S, Copenhagen, except that the instrument shown here is also intended to make potassium determinations. A similar blood gas measuring instrument is disclosed in the specification of U.S. Pat. No. 3,874,850.

Figure 7:
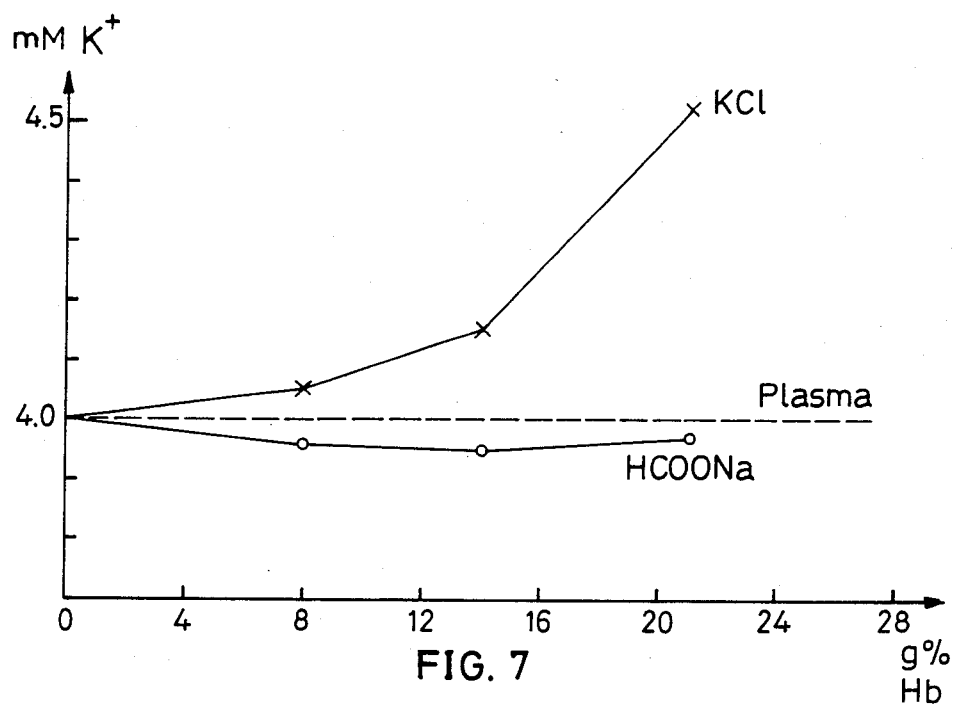
FIG. 7 is a graphic representation of the $K^+$-concentration, calculated in a measuring instrument, of a blood sample and the corresponding plasma as a function of the erythrocyte content of the sample, determined using a KCl salt bridge and a HCOONa salt bridge, respectively.
Figure 8:
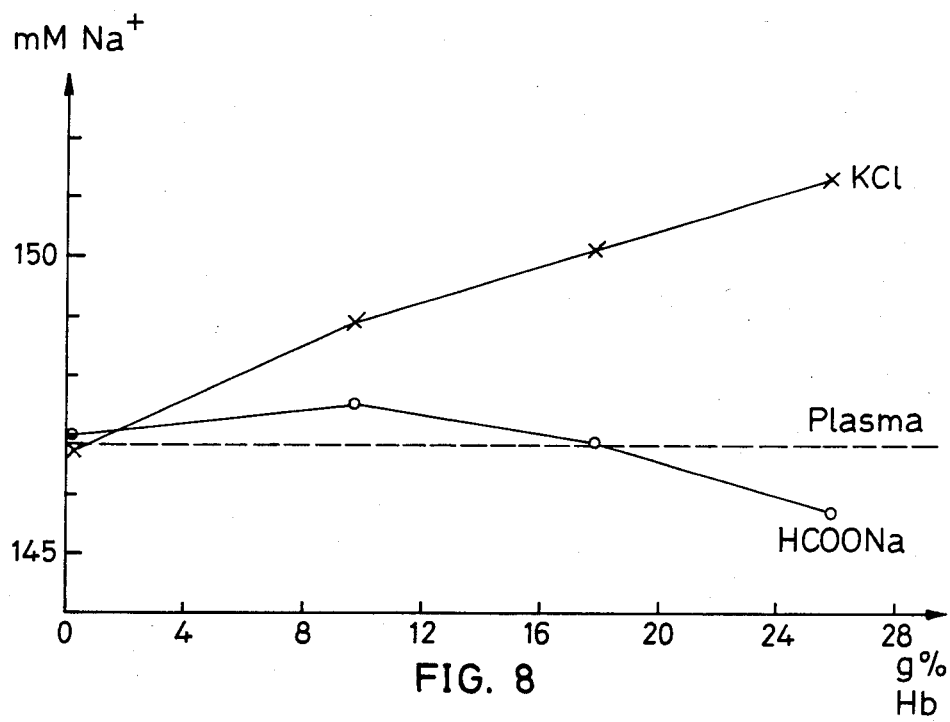
FIG. 8 is a graphical representation of the $Na^+$-concentration, calculated in another measuring instrument, of a blood sample and the corresponding plasma as a function of the erythrocyte content of the sample, determined using a KCl salt bridge and a HCOONa salt bridge, respectively.

FIGS. 7 and 8 are graphic representations of the measuring results obtained in Examples 3 and 2, respectively.

EXAMPLE 1

Preparation of Samples of Varying Erythrocyte Content

A portion of heparinized whole blood was centrifuged so that it was divided into a plasma phase and a erythrocyte concentrate. Then the two phases were mixed in various proportions, and the hemoglobin content was determined by a measuring instrument of the type OSM2 produced by RADIOMETER A/S, Copenhagen. In this measuring instrument (generally described in U.S. Pat. No. 3,972,614), the blood sample is hemolyzed, and the hemoglobin content found will be a measure of the erythrocyte content of the sample.

Samples of a hemoglobin content varying between 0 and about 28 g% were prepared in this manner.

EXAMPLE 2

Determination of Suspension Effect in Potentiometric Determination of Sodium 4 prototype measuring instruments of the type shown in FIGS. 1-5 were used.

From the same portion of blood, sample portions of an erythrocyte content of 4 levels were prepared according to the method indicated in Example 1. The hemoglobin content of the four sample portions was determined to be 0.2, 9.7, 17.8 and 25.8 g% respectively by means of an OSM2 instrument in the manner indicated in Example 1.

In two of the four prototype instruments, 2.7M KCl was used as salt bridge liquid and in the two others, 4M HCOONa was used as salt bridge liquid. From each of the four sample portions with different erythrocyte levels, 4 samples were taken for each instrument, i.e. totally 4×4 samples for each level.

On the basis of the values read on the instruments for the sodium concentration, the following results were obtained:

TABLE 1

| Hb (g %) | KCl salt bridge | | HCOONa salt bridge | |
|---|---|---|---|---|
| | $Na^+$ (mM) | SD (mM) | $Na^{30}$ (mM) | SD (mM) |
| 0.1 | 146.7 | 0.52 | 147.0 | 0.49 |
| 9.7 | 148.9 | 0.81 | 147.5 | 0.70 |
| 17.8 | 150.1 | 0.54 | 146.9 | 0.51 |
| 25.8 | 151.3 | 2.04 | 145.7 | 1.52 |

The calculated values of the $Na^+$-concentration reflecting the electrode potential, it is clearly seen from the measuring results in Table 1 and from the graphic representation thereof in FIG. 8 that the dependence of the electrode potential on the erythrocyte content of the sample is much lower when a HCOONa bridge is used than when a KCl salt bridge is used.

EXAMPLE 3

Determination of Suspension Effect In Potentiometric Determination of Potassium 4 prototype measuring instruments of the type shown in FIG. 6 were used.

From the same portion of blood, plasma and sample portions of an erythrocyte content of 3 levels were prepared according to the method described in Example 1.

The hemoglobin content of the three sample portions was determined to be 8, 14 and 21 g% respectively by means of an OSM2 instrument as described in Example 1.

In the two prototype instruments, 2.7M KCl was used as salt bridge liquid, and in the two others, 4M HCOONa was used as salt bridge liquid. The difference between the blood values and the corresponding plasma values, $\Delta_{Blood\ Plasma}$, in the potassium measurement appears from the table shown below. In this connection, it is be noted that the $K^+$-level of plasma is normally 4.0 mM.

TABLE 2

| Hb (g %) | KCl salt bridge | | | HCOONa salt bridge | | |
|---|---|---|---|---|---|---|
| | $\Delta_{Blood\ Plasma}$ | SD | n | $\Delta_{Blood\ Plasma}$ | SD | n |
| 8 | 0.05 | 0.04 | 4 | −0.04 | 0.01 | 4 |
| 14 | 0.15 | 0.04 | 3 | −0.03 | 0.01 | 4 |
| 21 | 0.52 | 0.08 | 3 | −0.03 | 0.02 | 4 |

The results in Table 2 and the graphic representation thereof in FIG. 7 clearly show that the dependence of the electrode potential on the erythrocyte content of the sample is much lower when a HCOONa salt bridge is used than when a KCl salt bridge is used.

We claim:

1. A method for the determination of the concentration of an ion in a sample of blood or blood liquid, using a measuring chain comprising an ion-sensitive indicator electrode and a reference electrode in which the ion-sensitive indicator electrode is brought into contact with the sample and the reference electrode is brought into contact with a salt bridge liquid which, through a liquid junction, is in contact with the sample, the salt bridge liquid used containing $Na^+$-ions and $HCOO^-$-ions.

2. A method as claimed in claim 1 wherein the salt bridge liquid contains $Na^+$-ions and $HCOO^-$-ions in substantially equimolar amounts in a concentration of more than or equal to 1M.

3. A method as claimed in claim 2 wherein the salt bridge liquid contains $Na^+$-ions and $HCOO^-$-ions in substantially equimolar amounts in a concentration of more than or equal to 1.5M.

4. A method as claimed in claim 2 wherein the salt bridge liquid contains $Na^+$-ions and $HCOO^-$-ions in substantially equimolar amounts in a concentration of about 4M.

5. A method as claimed in claims 1 wherein the ion whose concentration is determined is $K^+$, $Na^+$, $Ca^{++}$, $Mg^{++}$, $Li^+$, $H^+$, $HCO_3^-$ or $Cl^-$.

6. A method as claimed in claim 1, wherein the salt bridge solution consists essentially of an aqueous about 4M solution of HCOONa.

* * * * *